(12) United States Patent
Akiba

(10) Patent No.: US 7,645,231 B2
(45) Date of Patent: Jan. 12, 2010

(54) ENDOSCOPIC FLUID SUPPLY CONDUIT SYSTEM

(75) Inventor: Haruo Akiba, Saitama (JP)

(73) Assignee: Fujinon Corporation, Saitama (JP)

( * ) Notice: Subject to any disclaimer, the term of this patent is extended or adjusted under 35 U.S.C. 154(b) by 566 days.

(21) Appl. No.: 10/800,641

(22) Filed: Mar. 16, 2004

(65) Prior Publication Data
US 2004/0193017 A1  Sep. 30, 2004

(30) Foreign Application Priority Data
Mar. 28, 2003  (JP) ............................. 2003-091938

(51) Int. Cl.
*A61B 1/00* (2006.01)
(52) U.S. Cl. ................... 600/154; 600/132; 600/153; 600/155; 600/156; 600/157; 600/158; 600/159
(58) Field of Classification Search .............. 600/132, 600/154–159
See application file for complete search history.

(56) References Cited

U.S. PATENT DOCUMENTS

| | | | | |
|---|---|---|---|---|
| 4,205,683 A | * | 6/1980 | O'Neill | 604/99.02 |
| 4,412,531 A | * | 11/1983 | Chikashige | 600/104 |
| 4,548,197 A | * | 10/1985 | Kinoshita | 600/158 |
| 5,413,561 A | * | 5/1995 | Fischell et al. | 604/167.01 |
| 5,871,441 A | * | 2/1999 | Ishiguro et al. | 600/133 |
| 6,425,535 B1 | | 7/2002 | Akiba | |
| 6,569,087 B2 | * | 5/2003 | Naito et al. | 600/156 |

FOREIGN PATENT DOCUMENTS

JP          10-234658          9/1998

* cited by examiner

*Primary Examiner*—Matthew J Kasztejna
(74) *Attorney, Agent, or Firm*—Oblon, Spivak, McClelland, Maier & Neustadt, L.L.P.

(57) ABSTRACT

An endoscopic fluid supply conduit system for use with an endoscope having an insertion tube and a universal cable connected to and from a manipulating head assembly. A fluid conduit is provided internally of the insertion tube to supply a fluid from a fluid feed port on the manipulating head assembly toward a fluid jet injection port feed port which is provided on a rigid tip end section at the fore distal end of the insertion tube. In addition, a second fluid conduit is provided internally of the universal cable and toward the manipulating head assembly. A fluid supply channel selector is provided at the fluid feed port to which a fluid feed adaptor is to be disconnectibly connected. The fluid supply channel selector is adapted to block a fluid flow toward the second fluid conduit when a fluid is supplied to the first fluid conduit from the fluid feed port on the manipulating head assembly, and to bring the second fluid conduit into communication with the first fluid conduit when the fluid feed port on the manipulating head assembly is closed.

7 Claims, 5 Drawing Sheets

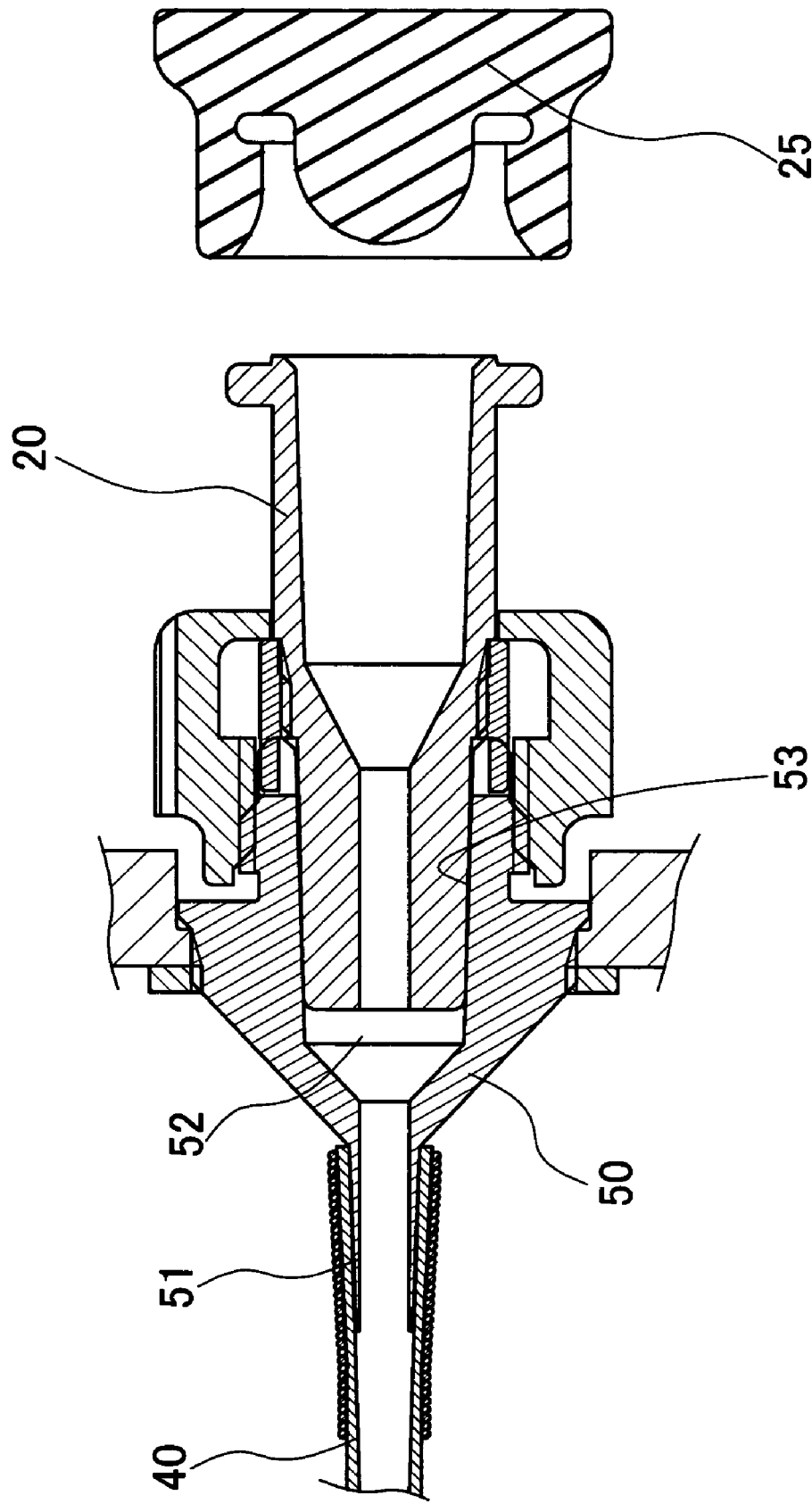

ENDOSCOPIC FLUID SUPPLY CONDUIT SYSTEM

BACKGROUND OF THE INVENTION

1. Field of the Art

This invention relates to a fluid supply conduit system suitable for use on medical endoscopes in charging and discharging a fluid to and from a body cavity, and more particularly to an endoscopic conduit system capable of supplying a fluid selectively either from a fluid supply source connected to a fluid feed port on a manipulating head assembly of an endoscope or from a fluid supply source connected to a universal cable of the endoscope.

2. Prior Art

Generally, medical endoscopes are largely constituted by a manipulating head assembly to be gripped and manipulated by an operator for controlling various endoscopic operations, an elongated insertion tube connected to a front side of the manipulating head assembly for insertion into a body cavity of a patient, and a universal cable led out on the rear side of the manipulating head assembly. The universal cable is disconnectibly connectible at least to a light source to transmit illumination light to the fore distal end of the insertion tube through a light guide. In addition to the light guide, various channels and passages are provided internally of the endoscope.

As for example of internal passages or channels, in many cases the so-called biopsy channel is provided in endoscopes to permit insertion of forceps or other biopsy or surgical instruments. The biopsy channel extends through the endoscope toward an exit opening which is opened at the distal end of the insertion tube. In addition, a suction channel is provided for aspiration of body fluids or the like. Normally, a suction channel is provided within an endoscope in communication with the biopsy channel. An aspirator with a vacuum pump device is connected to the other proximal end of the suction channel at the time of aspiration. A suction valve which is provided on the manipulating head assembly of the endoscope is connected to the suction channel and is manipulated by an operator at the time of starting or ending aspiration.

Further, a cleaning fluid supply channel is provided in the endoscope for the purpose of supplying cleaning fluids to be used in cleaning or washing an observation window which is provided at the fore distal end of the insertion tube. The cleaning fluid normally consists of a cleaning liquid (normally cleaning water) and compressed air. When an observation window is contaminated, a cleaning liquid is spurted toward the observation window to wash away contaminants therefrom. Thereafter, compressed air is supplied and blasted against the observation window to remove droplets of the cleaning liquid. Thus, for this purpose, a liquid feed channel and an air feed channel are provided in the endoscope. An air/water feed valve which is provided on the manipulating head assembly of the endoscope is operated by an operator at the time of supplying a cleaning liquid and compressed air to the liquid and air feed channels. The liquid feed channel and the air feed channel are joined together in the vicinity of the fore distal end of the insertion tube and connected to a spout nozzle which is directed toward the observation window. The air/water feed valve is put in a liquid feed position, whereupon a cleaning liquid is supplied to the spout nozzle and spurted toward the observation window. In the next place, the air/water feed valve is put in an air feed position, whereupon a jet of compressed air is spurted out from the nozzle. Thus, an observation window at the fore distal end of the endoscopic insertion tube can be washed clean without necessitating one to extract the insertion tube each time when it is found to be contaminated.

Further, in addition to the channels for the observation window cleaning operations, some endoscopes are provided with a fluid jet injection channel for injecting a jet of water toward an intracavitary wall under high pressure for washing purposes or for sprinkling a pigment on an intracavitary wall or for feeding or circulating a cleaning liquid to internal portions. Such a jet injecting channel is connected to an injection port which is opened at the fore distal end of the insertion tube to inject a cleaning water or a medicinal liquid.

In this connection, it has been the usual practice to employ a pump for supplying a large quantity of fluids to the injection port of the fluid jet injection channel from a supply tank. At this time, the other end of the channel is connected to a fluid supply tank and a pump. Since a universal cable is led out from the manipulating head assembly, from the standpoint of maneuverability of the manipulating head assembly, it is rather desirable to pass the fluid jet injection channel through the universal cable. However, in some cases the pump pressure is found insufficient to supply a fluid under a predetermined pressure. In this regard, it has been known in the art to boost the fluid supply pressure with a fluid from a syringe at the time of injecting a fluid from a passage from a pressure feed means which is connected to the fluid jet injection channel, for example, as disclosed in Laid-Open Japanese Patent Application H11-32988.

The purposes of use of the fluid jet injection channel include not only supply of a large quantity of a cleaning or wash water but also supply of a small amount of a coloring matter or a pigment under high pressure. At the time of supplying a required amount of a fluid under high pressure, it is desirable to pump in the fluid from the side of the manipulating head assembly by an operator using a syringe or a similar pressure feed means. However, in the case of the above-mentioned prior art, a syringe or a pressure feed means which is set on the manipulating head assembly of the endoscope is used as an auxiliary means for boosting the pressure of a fluid which is supplied through a fluid supply channel on the side of the universal cable, and not used as means for supplying a fluid from the side of manipulating head assembly independently of a pump. It follows that other fluid feed means becomes necessary for supplying a small amount of a medicinal solution under high pressure. Namely, the fluid injection channel of the above-mentioned prior art is not suitable for use in such cases where a necessary amount of a fluid has to be supplied under a certain pressure according to judgements of an operator.

SUMMARY OF THE INVENTION

With the foregoing situations in view, it is an object of the present invention to provide an endoscopic fluid supply conduit system which makes it possible to supply a fluid into a body cavity selectively either from a fluid supply source which is detachably attached to a manipulating head assembly of an endoscope or from a fluid supply source which is connected to a universal cable of the endoscope.

It is another object of the present invention to provide an endoscopic fluid supply conduit system which permits to supply a fluid selectively through one of two supply channels, one of which supply channels is suitable for use at the time of injecting a fluid into a body cavity under uniform pressure and at a constant flow rate while the other one is suitable for use in injecting a fluid under a desired pressure and at a desired flow rate.

It is still another object of the present invention to provide an endoscopic fluid supply conduit system which permits to supply a fluid selectively either from a manipulating head assembly or from a universal cable of an endoscope without increasing the diameter of the insertion tube.

In accordance with the present invention, the above-stated objectives are achieved by the provision of an endoscopic fluid supply conduit system for an endoscope having an insertion tube and a universal cable connected to and from a manipulating head assembly, the fluid supply conduit system comprising: a first fluid conduit extended from the manipulating head assembly and through the insertion tube toward a fluid injection port provided on a rigid tip end section at the fore distal end of the insertion tube; a fluid feed port provided on the manipulating head assembly in communication with the first fluid conduit and arranged to permit connection thereto of a fluid feed adaptor; a second fluid conduit provided internally of the universal cable and communicable with the first fluid conduit within the manipulating head assembly; and a fluid supply channel selector means adapted to block a fluid flow from the second fluid conduit to the first fluid conduit at the time of feeding a fluid from the fluid feed port to the first fluid conduit, while permitting a fluid flow from the second fluid conduit to the first fluid conduit when the fluid feed port is closed.

According to the present invention, two fluid supply channels are provided internally of an endoscope to supply a fluid to a fluid jet injection port which is opened on a rigid tip end section at the fore distal end of the insertion tube of the endoscope. With the fluid supply conduit system according to the present invention, it is possible to select fluid supply either from a fluid feed port which is provided on a manipulating head assembly of the endoscope or from and through a universal cable of the endoscope. That is to say, the fluid supply conduit system is provided with first and second fluid conduits which can be selected by the fluid supply channel selector means. When a fluid is fed into the first fluid conduit through the fluid connection port, the supplied fluid is prevented from flowing into the second fluid conduit. On the other hand, when a fluid is supplied to the endoscope from the side of the second fluid conduit, the supplied fluid is prevented from flowing out of the fluid feed port on the manipulating head assembly of the endoscope.

In a preferred form of the present invention, the fluid supply channel selector means is constituted by a mouth piece which is fixedly fitted in the fluid feed port on the manipulating head assembly of the endoscope, the mouth piece having a first connection port provided at an inner axial end for connection of the first fluid conduit and a second connection port provided at one side for connection of the second fluid conduit. When a fluid feed adaptor is fitted into the mouth piece, the second connection port is closed by the fluid feed adaptor. When the fluid feed adaptor is removed from the mouth piece and instead a plug member is fitted to close an outer open end of the mouth piece, the first and second fluid conduits are communicated with each other, permitting fluid supply from the second to the first fluid conduit while preventing fluid leaks through the mouth piece.

In another preferred form of the present invention, the second fluid conduit is joined with a halfway point of the first fluid conduit within a casing of the manipulating head assembly, and a reverse flow checking valve is inserted in the second fluid conduit at the junction point with the first fluid conduit to prevent a fluid flowing in a reverse direction toward the second fluid conduit from the side of the first fluid conduit.

The above and other objects, features and advantages of the present invention will become apparent from the following particular description of the invention, taken in conjunction with the accompanying drawings which show by way of example some preferred embodiments of the present invention. Needless to say, the present invention is not limited to the particular forms shown in the drawings.

BRIEF DESCRIPTION OF THE DRAWINGS

In the accompanying drawings:

FIG. 5 is a schematic sectional view of a mouth piece employed in the second embodiment of the invention.

DESCRIPTION OF PREFERRED EMBODIMENTS

Figure 1:
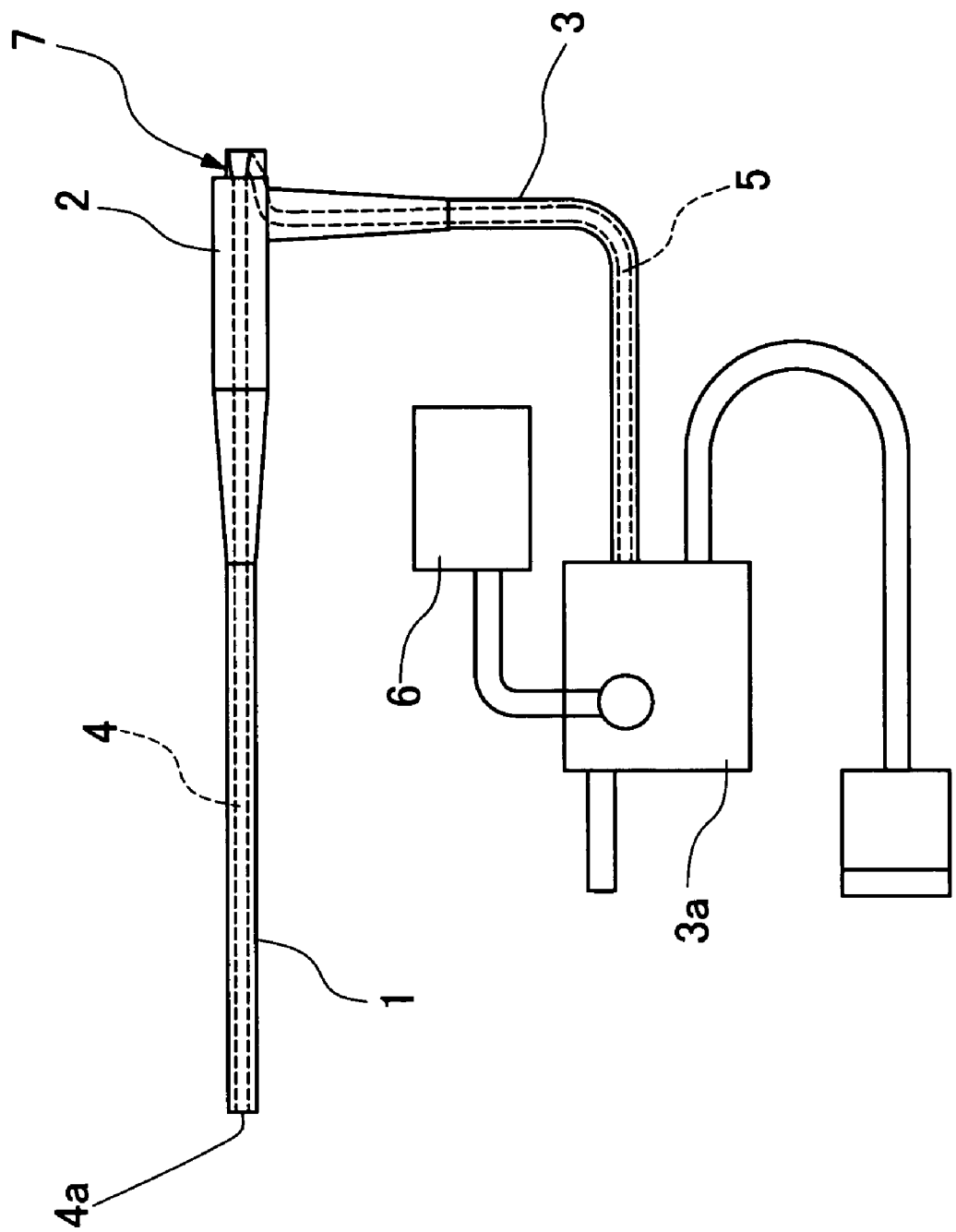
FIG. 1 is a schematic illustration of an endoscope incorporating an endoscopic fluid supply conduit system according to the present invention.

Hereafter, the present invention is described more particularly by way of its preferred embodiments with reference to the accompanying drawings. Referring first to FIG. 1, there is schematically shown general layout of an endoscope. In this figure, 1 is shown an insertion tube 1, a manipulating head assembly 2 and a universal cable 3 of the endoscope. As well known in the art, illumination and observation windows, an exit opening of a biopsy channel and an observation window washing nozzle are provided at the fore distal end of the insertion tube 1. In this case, the endoscope is provided with a fluid jet injection system.

The fluid supply conduit system is provided internally of the insertion tube 1 and the manipulating head assembly 2 of the endoscope. The fluid supply conduit system includes a first fluid conduit 4 which is extended internally through the insertion tube 1, and a second fluid conduit 5 which is extended internally through the universal cable and to the manipulating head assembly 2 of the endoscope. Further, the second fluid conduit 5 is led out from a connector portion 3a of the universal cable 3 and connected to a fluid feed device 6, which is composed of a fluid supply tank and a pump. A fluid supply channel selector means 7 is provided on the manipulating head assembly 2 thereby to select a fluid supply channel between a first supply channel which supplies a specified fluid from the manipulating head assembly 2 through the first conduit 4 and a second supply channel which supplies a specified fluid from the fluid feed device 6 through the first and second conduits 4 and 5.

Figure 2:
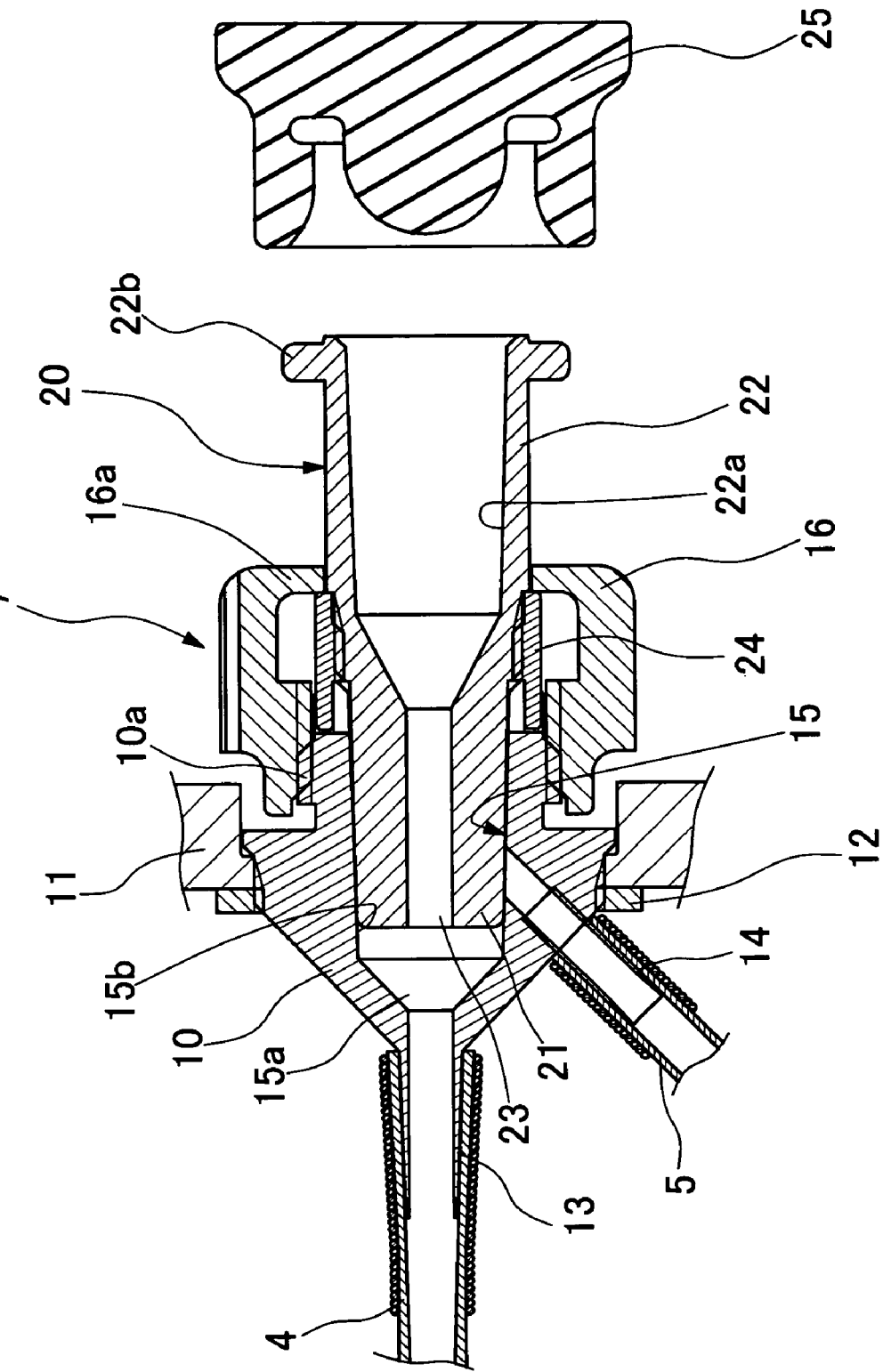
FIG. 2 is a schematic sectional view of a fluid supply channel selector means in a first embodiment of the present invention, with a fluid feed adaptor fitted on the channel selector means.
Figure 3:
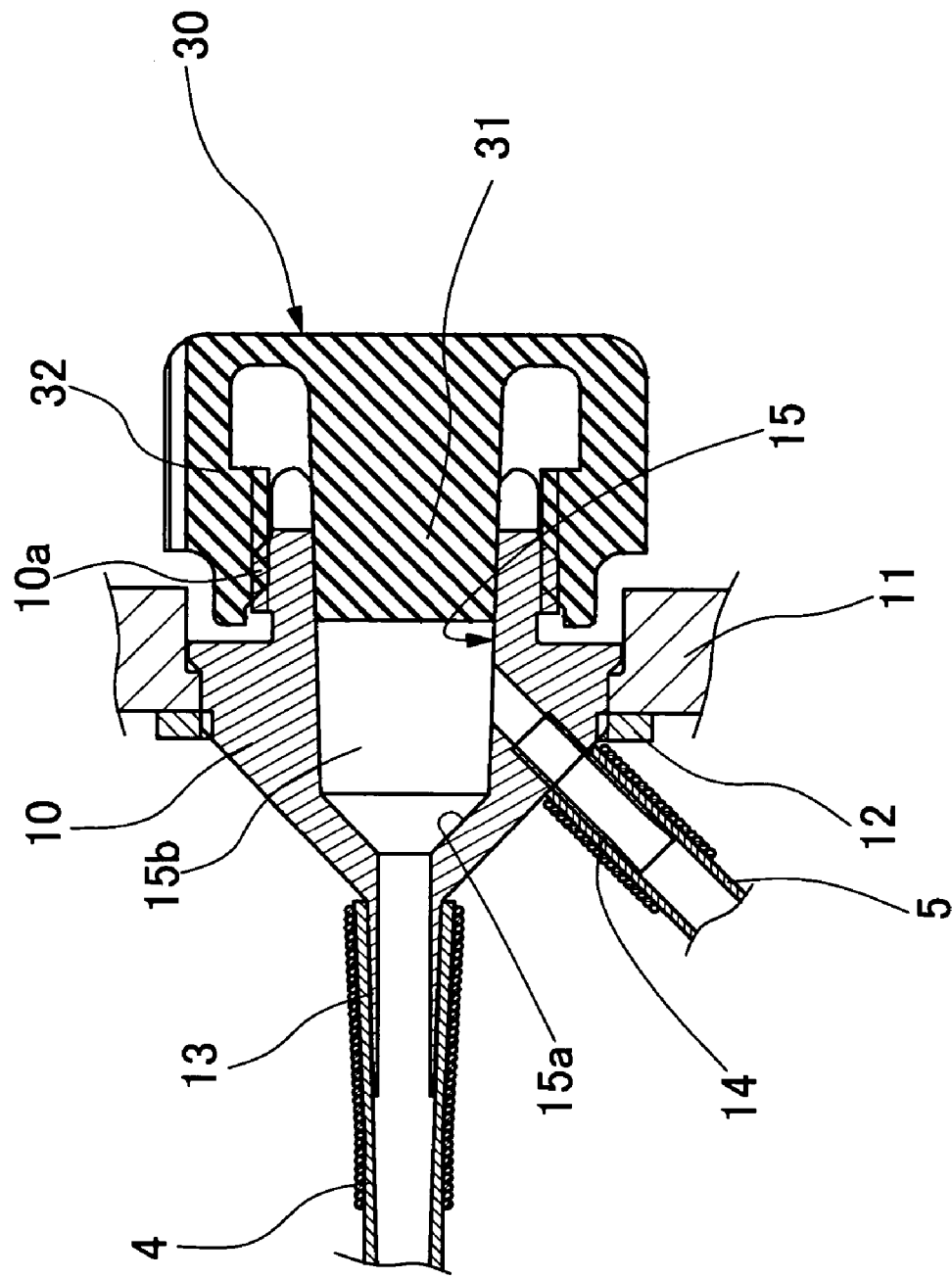
FIG. 3 is a schematic sectional view of the channel selector means of FIG. 2 and a plug member which is fitted on the channel selector means.

Shown schematically in FIGS. 2 and 3 is the construction of the fluid supply channel selector means 7. In these figures, indicated at 10 is a mouth piece which is securely fixed to a casing 11 of the manipulating head assembly 2 by a nut 12 to provide a fluid feed port on the proximal side of the manipulating head assembly 2, that is to say, on the side away from the front side to which the insertion tube 1 connected. The mouth piece 10 is provided with a first connecting portion 13 in the form of a tube at its fore end to function as a connection port for the first fluid conduit 4, and a second connecting portion 14 in the form of a tube which is provided on a lateral side of the mouth piece as a connection port for the second fluid conduit 5. These connection ports 13 and 14 are both opened to an axial receptacle bore 15 in the mouth piece 10. The receptacle portion 15 is open on the outer side of the manipulating head assembly 2. Either a fluid feed adaptor 20 or a closure plug member 30 of a resilient material is detachably attached to the outer open end of the receptacle portion 15.

The first connection port 13 is opened to a fore end portion of the receptacle bore 15, while the second connection port 14 is opened to a side portion of the receptacle bore 15. In this instance, the diameter of the receptacle bore 15 is gradually reduced in the inward direction, providing a reduced diameter portion 15a at the fore end in communication with the first connection port 13 which is projected inward continuously from the inner end of the mouth piece 10. On the proximal side, the reduced diameter portion 13 is moderately tapered to provide a Luer-Lok taper portion 15b. The second connection port 14 is in communication with the Luer-Lok portion 15b of the receptacle bore 15.

The fluid feed adaptor 20 to be detachably fitted in the receptacle bore 15 of the mouth piece 10 has a construction as shown in FIG. 2. More specifically, the fluid feed adaptor 20 is provided with a tapered fore end portion 21 the circumferential surface of which is tapered with a corresponding taper angle relative to the Luer-Lok taper portion 15b of the receptacle bore 15, and a connector portion 22. The tapered fore end portion 21 of the fluid feed adaptor 20 is inserted into the receptacle bore 15 beyond and forward of a position where the second connection port 14 is opened to the Luer-Lok taper portion 15b of the receptacle bore 15. On the other hand, for example, the connector portion 22 of the fluid feed adaptor 20 is arranged in a shape suitable for connection of a fluid feed means like a syringe. Therefore, the fluid feed adaptor 20 is provided with a Luer-Lok taper surface 22a on its inner periphery, and a flange 22b at its outer proximal end. When a syringe or a similar fluid feed means is attached to the fluid feed adaptor 20, a fluid can be fed under pressure from the fluid supply passage 23 to the first fluid conduit 4 which is connected to the first connection port 13 of the mouth piece 10.

An external screw 10a is provided on the circumferential surface of the mouth piece 10 on the outer side of the casing 11, for the purpose of retaining in a stabilized state the fluid feed adaptor 20 which is attached to the mouth piece 10, and at the same time for the purpose of holding in a hermetically closed state the second connection port 14 which is opened to the Luer taper portion 15b. On the other hand, a stopper ring 24 is threaded on an external screw on provided on the fluid feed adaptor 20 in a transitional portion between the fore tapered portion 21 and the connector portion 22, into abutting engagement with outer end face of the mouth piece 10. The stopper ring 24 is securely fixed in position on the fluid feed adaptor 20 by the use of an adhesive or other suitable means. A screw ring 16 is mounted between the stopper ring 24 and the flange portion 22b, in threaded engagement with an external screw portion 10a of the mouth piece 10. This screw ring 16 is provided with an inwardly turned portion 16a at its outer end and is thereby prevented from falling off the fluid feed adaptor 20.

Thus, the fluid feed adaptor 20 can be attached to the mouth piece 10 by tightening the screw ring 16 after inserting the tapered fore end portion 21 of the fluid feed adaptor 20 into the Luer taper portion 15b of the receptacle bore 15, whereupon, the stopper ring 24 is pushed in by the stopper portion 16a of the screw ring 16 until the tapered fore end portion 21 of the fluid feed adaptor 20 is brought into intimate contact with the Luer taper portion 15b of the receptacle bore 15 of the mouth piece 10. As a result, the fluid feed adaptor 20 fixedly attached to the mouth piece 10, hermetically closing the opening of the second connection port 14. Even when the fluid feed adaptor 20 is attached to the mouth piece 10, the closure plug member 25 is fitted on the connector portion 22 as long as no fluid feed means is connected thereto.

Shown in FIG. 3 is a plug member 30 to be attached to the mouth piece 10 in place of the fluid feed adaptor 20. The plug member 30 is made of a resilient material like rubber, and is provided with a cylindrical main body portion 31 which is adapted to be pushed into the receptacle bore 15 of the mouth piece 10 to a predetermined degree, and a tubular fastening skirt portion 32 which is formed around the cylindrical main body portion 31. Accordingly, the outer open end of the receptacle bore 15 of the mouth piece 10 is closed upon attaching the plug member 30 to the mouth piece 10. In the Luer taper portion 15b of the receptacle bore 15, the main body portion 31 of the plug member 30 is stopped at a position short of the second connection port 14. As a consequence, the second connection port 14 is communicated with the first connection port 13, and a fluid from the second fluid conduit 5 is supplied to the first fluid conduit 4 and spurted out from the fluid jet injection port 4a at the fore distal end of the insertion tube 1.

In the above-described conduit system, the plug member 30 is fitted on the mouth piece 10 when no fluid is supplied from a syringe on the side of the manipulating head assembly 2. It follows that, unless the fluid feed device 6 is actuated, no fluid is supplied to the first and second fluid conduits 4 and 5. If the pump of the fluid feed device 6 is started in this state, a required fluid is fed to the second fluid conduit 5 from the fluid feed device 6 under a rated pump pressure and at a constant flow rate. Through the second connection port 14, the fluid is allowed to flow into the receptacle bore 15 of the mouth piece 10, and supplied to the first fluid conduit 4 from the first connection port 13 to spurt a jet of a fluid, for example, a jet of cleaning water into a body cavity for cleaning purposes. This sort of operation can be carried out not only by an operator but also by a nurse or assistant personnel on demand of an operator.

On the other hand, in case a syringe is used as a fluid supply source, the plug member 30 removed from the mouth piece 10 and the fluid feed adaptor 20 is attached to the mouth piece 10 before or after introducing the endoscopic insertion tube 1 into a body cavity. In such a case, a lid member 25 of resilient material is fitted on the connector portion 22 of the fluid feed adaptor 20 to keep the outer open end of the fluid feed adaptor 20 in a hermetically closed state until actually starting supply of a fluid. Then, when it becomes necessary to supply a fluid into a body cavity, the lid member 25 is removed from the fluid feed adaptor 20 and instead a syringe is connected to the connector portion of the fluid feed adaptor 20. Thus, a suitable amount of a fluid, for example, a suitable amount of coloring agent can be sent into a body cavity under a desired pressure and at a suitable time point according to judgements of an operator.

After use, the first and second fluid conduits 4 and 5 of the endoscope have to be washed clean. At the time of washing these conduits, the fluid feed adaptor 20 and the plug member 30 are removed from the mouth piece 10. The first and second fluid conduits 4 and 5 are joined through the mouth piece 10 but are separately connected to the first and second connecting portions 13 and 14 of the mouth piece 10. Besides, both of the first and second fluid conduits 4 and 5 have no branches or junction points so that they can be washed easily and completely by the use of a brush or the like.

Figure 4:
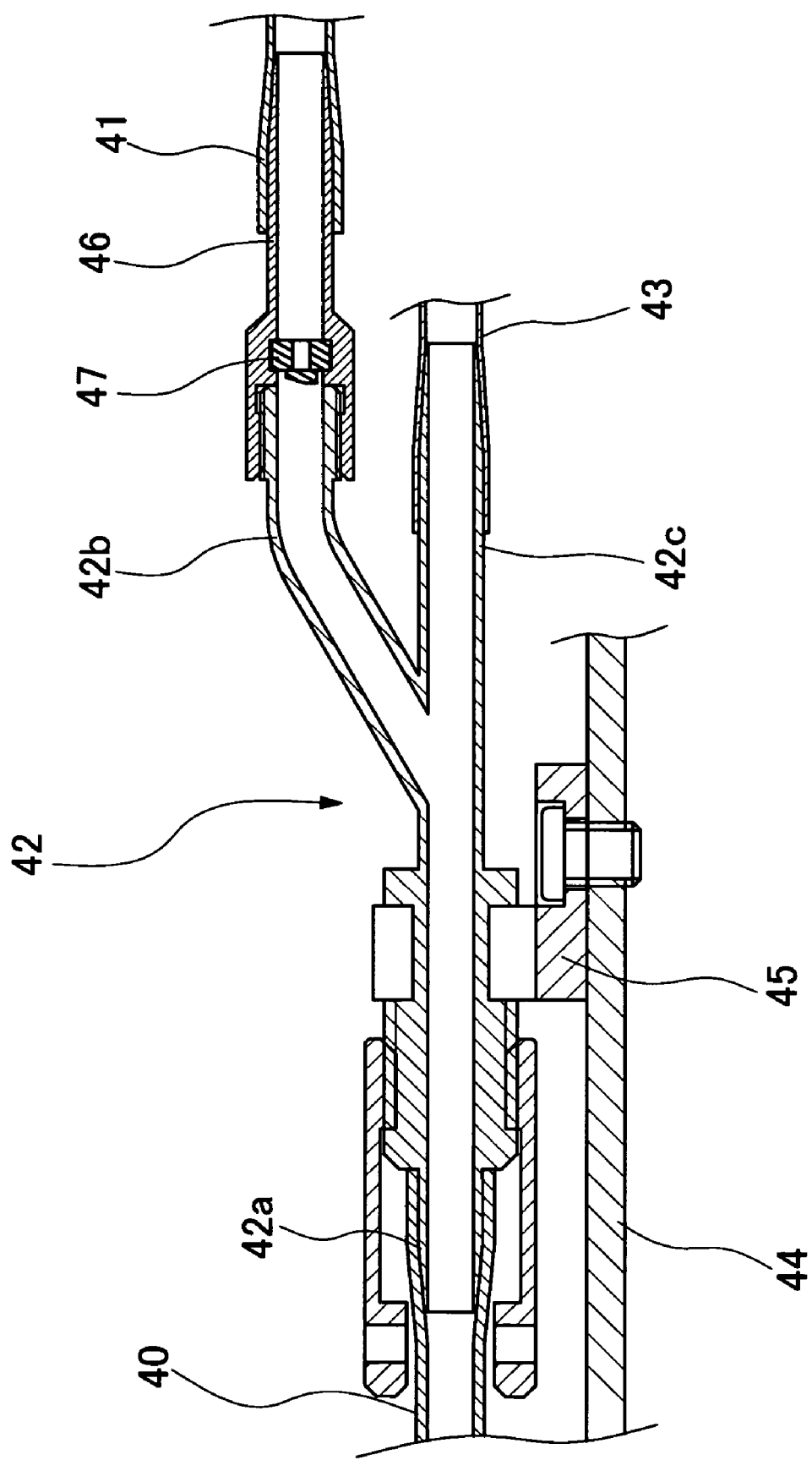
FIG. 4 is a schematic sectional view of a forked junction pipe member employed as a channel selector means in a second embodiment of the present invention, the junction pipe member being connected with first and second fluid conduits.

Turning now to FIGS. 4 and 5, there is shown a second embodiment of the present invention. In this embodiment, the first and second fluid conduits 4 and 5 are joined together through a junction pipe member which is provided within the casing of the manipulating head assembly, preventing fluid flow into the second fluid conduit 5 from the side of the first fluid conduit 4.

In FIG. 4, indicated by reference number 40 is a first fluid conduit leading to a fluid jet injection port at the fore distal end of the insertion tube of the endoscope, and by reference number 41 is a second fluid conduit which is connected to a fluid feed device through the universal cable of the endoscope. These first and second fluid conduits 40 and 41 are connected to first and second connecting portions 42a and 42b of a junction pipe member 42, respectively. The junction pipe member 42 is further provided with a third connecting portion 42c which is constantly in communication with the first fluid conduit 40. Connected to the third connecting portion 42c is one end of a communicating conduit 43 the other end of which is connected from a mouth piece 50 provided on the rear side of the manipulating head assembly of the endoscope. Accordingly, this communicating conduit 43 constitutes part of the first fluid conduit 40, and the other end which is connected with the mouth piece forms a connecting end. The forked junction pipe member 42 is securely anchored in position by a holder member 45 which is fixedly mounted on a support plate 44 within a casing of the manipulating head assembly.

As seen in FIG. 5, the mouth piece 50 is arranged in a manner similar to the mouth piece 10 of the first embodiment shown in FIGS. 2 and 3. The mouth piece 50 is provided with a connection port 51 which corresponds to the first connection port of the mouth piece 10, but in this case the mouth piece 50 is not provided with a second connection port at its side portion. Since the mouth piece 50 is provided with a Luer taper portion 53 in its receptacle bore 52, a syringe or a similar fluid feed means can be connected to the mouth piece 50 directly or by way of a fluid feed adaptor 20 as shown in FIG. 2.

The second fluid conduit 41 is connected to the second connecting portion 42b of the junction pipe 42 not directly but through a reverse flow blocking or checking member 46. This reverse flow checking member 46 is in a tubular pipe-like form having one end thereof connected to the second fluid conduit 41 and the other end in threaded engagement with the second connecting portion 42b of the junction pipe member 42. Fitted internally of the reverse flow checking member 46 is a check valve 47 which permits a fluid flow into the junction pipe member 42 from the second fluid conduit 41, while blocking a fluid flow into the second fluid conduit 41 from the side of the junction pipe member 42.

With the arrangements as described above, it is possible to control the supply of a fluid in the same manner as in the first embodiment. Namely, when the fluid feed adaptor 20 is connected to the mouth piece 50 on a manipulating head assembly of a endoscope, a necessary amount of a fluid, for example, a necessary amount of a coloring agent can be send to the first fluid conduit 40 from a syringe or a similar fluid feed means which is connected to the fluid feed adaptor 20, and injected into a body cavity under a suitable pressure. In so doing, reverse flow of the supplied fluid toward the second fluid conduit 41 is prevented by the action of the check valve 47. Further, when the plug member 30 of FIG. 3 is fitted on the mouth piece or when the outer open end of the fluid feed adaptor 20 is closed with the lid member 25, a fluid can be supplied to the second fluid conduit 41 by actuating a fluid feed device which is connected to a proximal end portion of the universal cable, whereupon, the check valve 47 is pushed open by the supplied fluid pressure, and the fluid is supplied to the first fluid conduit 40 from the junction pipe member 42 and spurted into a body cavity from the fluid jet injection port at the distal end of the endoscopic insertion tube. Of course, there is no possibility of fluid leaks through the mouth piece 50 as long as it is closed with the plug member.

What is claimed is:

1. An endoscopic fluid supply conduit system suitable for use in an endoscope which comprises:
    a manipulating head assembly;
    an insertion tube connected at a fore end of said manipulating head assembly, and a universal cable being connected to and extending downwardly from said manipulating head assembly;
    a first fluid conduit extended from said manipulating head assembly and through said insertion tube toward an injection port provided on a rigid tip end section at a fore distal end of said insertion tube;
    a second fluid conduit provided internally of said universal cable and communicable with said first fluid conduit within said manipulating head assembly;
    a fluid feed port formed at a proximal side of said manipulating head assembly and a mouth piece fixedly fitted in said fluid feed port, said fluid feed port having an axial receptacle bore, a first connection port formed at an inner axial end of said mouth piece for connecting said first fluid conduit in communication with said receptacle bore and a second connection port provided at one side of said mouth piece for connecting said second fluid conduit in communication with said receptacle bore;
    said first fluid conduit being extended linearly from said axial receptacle bore toward said insertion tube, while said second fluid conduit being inclined with respect to a longitudinal axis of said axial receptacle bore;
    a fluid supply adaptor having an axially extended fluid supply passage to be attached to a fluid feed member to feed a fluid under pressure to said first fluid conduit, a tip end thereof being opened toward said first connection port and being adapted to be inserted into said mouth piece to block a fluid flow from said second fluid conduit to said first fluid conduit and to feed a fluid from said fluid supply passage to said first fluid conduit; and
    a plug member fitted in an outer open end of said receptacle bore of said mouth piece after removing said fluid supply adapter from said mouth piece to bring said second connection port into communication with said first connection port through said receptacle bore.

2. An endoscopic fluid supply conduit system as defined in claim 1, wherein said fluid feed port on said manipulating head assembly is provided on a side away from the side to which said insertion tube is connected.

3. An endoscopic fluid supply conduit system as defined in claim 1, wherein said mouth piece is arranged in such a way as to disconnectibly receive said fluid feed adaptor in said receptacle bore, and is communicated with said first fluid conduit at an inner axial end and with said second fluid conduit at a halfway position in the axial direction.

4. An endoscopic fluid supply conduit system as defined in claim 3, wherein said receptacle bore of said mouth piece is provided with a first tapered mating surface to be brought into fitting engagement with a second tapered mating surface provided on outer periphery of said fluid feed adaptor.

5. An endoscopic fluid supply conduit system as defined in claim 1, wherein said fluid feed adaptor is provided with a tapered mating surface mechanism to permit connection of at least one syringe configured to interface with a first tapered mating surface of the tapered mating surface mechanism, wherein each of the at least one syringe having a second tapered mating surface.

6. An endoscopic fluid supply conduit system as defined in claim 1, further comprising a lid member detachably attachable to said fluid supply adaptor to close outer open end of the latter.

7. An endoscopic fluid supply conduit system suitable for use in an endoscope which comprises:
   a manipulating head assembly;
   an insertion tube connected at a fore end of said manipulating head assembly, and a universal cable being connected to and extending downwardly from said manipulating head assembly,
   a first fluid conduit extended from said manipulating head assembly and through said insertion tube toward an injection port provided on a rigid tip end section at a fore distal end of said insertion tube;
   a second fluid conduit provided internally of said universal cable and communicable with said first fluid conduit within said manipulating head assembly;
   a fluid feed port formed at a proximal side of said manipulating head assembly and a mouth piece fixedly fitted in said fluid feed port, said fluid feed port having an axial receptacle bore, a first connection port formed at an inner axial end of said mouth piece for connecting said first fluid conduit in communication with said receptacle bore and a second connection port provided at one side of said mouth piece for connecting said second fluid conduit in communication with said receptacle bore;
   said first fluid conduit being extended linearly from said axial receptacle bore toward said insertion tube, while said second fluid conduit being inclined with respect to a longitudinal axis of said axial receptacle bore;
   a fluid supply adaptor having an axially extended fluid supply passage to be attached to a fluid feed member to feed a fluid under pressure to said first fluid conduit, a tip end thereof being opened toward said first connection port and being adapted to be inserted into said mouth piece to block a fluid flow from said second fluid conduit to said first fluid conduit and to feed a fluid from said fluid supply passage to said first fluid conduit; and
   a plug member fitted in an outer open end of said receptacle bore of said mouth piece after removing said fluid supply adapter from said mouth piece to bring said second connection port into communication with said first connection port through said receptacle bore,
   wherein said mouth piece is arranged in such a way as to disconnectibly receive said fluid feed adaptor in said receptacle bore, and is communicated with said first fluid conduit at an inner axial end and with said second fluid conduit at a halfway position in the axial direction,
   wherein said receptacle bore of said mouth piece is provided with a first tapered mating surface to be brought into fitting engagement with a second tapered mating surface provided on outer periphery of said fluid feed adaptor, and
   wherein said mouth piece is provided with an external screw on outer periphery thereof, while said fluid feed adaptor is provided with a stopper ring on outer periphery thereof for abutting engagement with outer end face of said mouth piece and fixedly fastened to said mouth piece by threading a screw ring onto said external screw on the outer periphery of said mouth piece.

* * * * *